United States Patent
Yarnall et al.

(10) Patent No.: US 6,559,440 B2
(45) Date of Patent: *May 6, 2003

(54) METHOD FOR CALIBRATING A RADIATION DETECTION SYSTEM

(75) Inventors: Stephen T. Yarnall, Poway, CA (US); Jerome E. Gormley, San Diego, CA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/027,759

(22) Filed: Dec. 21, 2001

(65) Prior Publication Data

US 2002/0063204 A1 May 30, 2002

Related U.S. Application Data

(63) Continuation of application No. 09/425,481, filed on Oct. 22, 1999, now Pat. No. 6,362,472.

(51) Int. Cl.[7] .............................. G01T 1/161; A61B 5/00
(52) U.S. Cl. ..................... 250/252.1; 600/436
(58) Field of Search ..................... 250/252.1, 363.09, 250/303; 600/436

(56) References Cited

U.S. PATENT DOCUMENTS

| | | |
|---|---|---|
| 4,782,840 A | 11/1988 | Martin, Jr. et al. |
| 4,801,803 A | 1/1989 | Denen et al. |
| 4,889,991 A * | 12/1989 | Ramsey et al. ........... 250/336.1 |
| 5,070,878 A | 12/1991 | Denen |
| 5,246,005 A | 9/1993 | Carroll et al. |
| 5,475,219 A | 12/1995 | Olson |
| 5,682,888 A * | 11/1997 | Olson et al. ............. 250/336.1 |
| 5,694,933 A | 12/1997 | Madden et al. |
| 5,732,704 A | 3/1998 | Thurston et al. |
| 5,813,985 A | 9/1998 | Carroll |
| 5,846,513 A | 12/1998 | Carroll |
| 5,916,167 A | 6/1999 | Kramer et al. |
| 5,928,150 A | 7/1999 | Call |
| 6,331,703 B1 | 12/2001 | Yarnall et al. |
| 6,362,472 B1 * | 3/2002 | Yarnall et al. ........... 250/252.1 |

OTHER PUBLICATIONS

Radiation And Detection And Measurement, Glenn F. Knoll, John Wiley and Sons, Inc. 1989, pp. 610–620.

* cited by examiner

*Primary Examiner*—Georgia Epps
*Assistant Examiner*—Richard Hanig
(74) *Attorney, Agent, or Firm*—Gerry S. Gressel

(57) ABSTRACT

An automatic and intuitive calibration method is provided for calibrating a radiation detection system for processing counts from a known radiation source. A probe is positioned near the radiation source, which may be the surgical injection site of a radionucleide. A control unit generates audible and/or visual feedback signals to cue the operator as to where to position the probe relative to the radiation source, in order to obtain a pulse frequency (count rate) in an optimal range for processing. The control unit then automatically identifies a peak energy level and sets an energy acceptance window having a mathematical relationship to the peak energy level, whereby the radiation detection system thereinafter processes only counts corresponding to energy levels falling within the energy acceptance window.

16 Claims, 6 Drawing Sheets

METHOD FOR CALIBRATING A RADIATION DETECTION SYSTEM

The present application is related to U.S. patent application Ser. No. 09/266,961 filed on Mar. 12, 1999 now U.S. Pat. No. 6,331,703, which is hereby incorporated herein by reference.

This continuation patent application claims priority to pending U.S. patent application Ser. No. 09/425,481, "Method for Calibrating a Radiation Detection System" filed Oct. 22, 1999 now U.S. Pat. No. 6,362,472.

FIELD OF THE INVENTION

The present invention relates, in general, to methods for processing signals from nuclear uptake probes for radiation detection and, more particularly, to methods of adjusting a control unit to calibrate a radiation detection system each time a new probe is used.

BACKGROUND OF THE INVENTION

Radioactive pharmaceuticals used in combination with radiation detection systems have been proven to be effective in locating radio labeled tissue within patients. These pharmaceuticals are also known as radionucleides and include solutions of Iodine 125, Iodine 131, and Phosphorous 32. Other radionucleides include monoclonal antibodies, peptides, and certain colloids labeled with radioactive isotopes such as Technetium-99. Once a radionucleide is introduced into a patient's body, it will tend to collect at targeted tissue sites, such as, for example, lymph node sites and such sites may be located by looking for concentrations of the radionucleide.

The mammalian lymphatic system has various interrelated functions, including circulating and modifying tissue fluid formed in capillary beds and removing cell debris and foreign matter. For certain cancers, neoplastic cells migrate and collect at regional nodes within an associated lymph drainage basin. Some cancers, such as those encountered in the breast, will evidence somewhat predictable nodal involvement. The axillary lymph node region is the principal site of regional metastasis from carcinoma of the breast, and approximately 40% of patients have evidence of spread to the axillary nodes. In some approaches to the disease, these axillary nodes are removed as a form of therapy.

Sentinel node biopsy is a less invasive alternative to lymph node dissection in diagnosing metastasis of breast cancer tumors. The principle of sentinel node biopsy is that neoplastic cells detaching from the primary tumor are most likely to be held by the sentinel node, which is the first lymph node to receive lymph from the involved area and the most likely site of early metastasis. If the sentinel node is free of cancer, it is highly probable that all of the other nodes are free of cancer cells. This knowledge helps the physician in staging the disease.

Thus, it is important to identify the sentinel node when trying to determine whether cancer has metastasized. Detection of a sentinel node may be achieved by using a gamma ray detection probe intra-operatively to assist surgeons in locating tissue tagged with a radionucleide. U.S. Pat. No. 5,732,704 to Thurston et al discloses a radiation based method for locating and differentiating sentinel nodes. The method described is used to identify a sentinel lymph node located within a grouping of regional nodes at a lymph drainage basin connected to neoplastic tissue. A radionucleide is injected near the neoplastic tissue and migrates along a lymph duct toward the drainage basin containing the sentinel node. A hand-held, radiation detection probe is moved along the lymph duct while the operator observes a graphical readout of count rate amplitudes to determine when the probe is aligned with the duct. The region containing the sentinel node is identified when the count rate at the probe substantially increases. Following incision, the probe is maneuvered using a sound output to establish increasing count rate thresholds. The probe is then moved incrementally until the probe is adjacent to the sentinel node, which then may be surgically removed. The visual and audio signals used by the surgeon are generated by the signal processing portion of the radiation detection system, which may be referred to as the control unit control unit. The control unit is connected to the handheld probe to form the radiation detector system.

The success of using a method such as disclosed in U.S. Pat. No. 5,732,704 depends upon the reliability of the hand-held radiation detection probe and the calibration between the probe and the control unit. The probe generally operates at room temperature and is designed to detect very low levels of gamma radiation. The gamma radiation emitted from the sentinel node may be masked by background noise such as cosmic radiation, thermal noise, and capacitively or piezoelectrically induced noise resulting from manipulation of the probe itself. One function of the control unit is to filter gamma radiation emitted by the radio tagged tissue from background noise and other sources of gamma radiation, including Compton scatter.

Gamma ray detection probes may include a high-Z semiconductor (such as CdZnTe or CdTe) or a scintillation crystal such as sodium-iodide (NaI) which is coupled with a small photo multiplier tube. U.S. patent application Ser. No. 09/066,545, filed on Apr. 24, 1998 now abandoned, describes a relatively low-cost radiation detection probe. The probe integrates a silicon photodiode detector (with or without a scintillation assembly) with amplifiers, interface electronics, and radiation shielding, into one compact radiation probe assembly. The probe assembly uses relatively low voltages, has relatively few electrical connections, is relatively easy to manufacture, and is low-cost. The disclosed radiation detection probe is particularly useful for detecting radionucleides during lymphatic mapping and localization of a sentinel node.

Despite recent advances to lower the cost of manufacture and use of radiation detection probes, it is still necessary to insure that the electronic signal generated by the probes are correctly interpreted by the control unit. Careful attention to manufacturing tolerances and the use of specially selected electronic components may ensure adequate calibration between probes and adequate stability after the probes leave the factory, thus ensuring that the output for a given input is relatively constant across a selection of probes and relatively stable over time. Of course, such manufacturing tolerances and special electronics add significant cost. Lower cost probes, on the other hand, may be manufactured to wider tolerances and utilize less expensive electronics, making them less consistent probe to probe and more likely to lose calibration after leaving the factory. One particularly important characteristic of radiation detection probes is the signal output level generated by a predetermined signal input level. For example, one probe may generate an electronic pulse output of 5.1 volts when a gamma ray having an energy level of 140.5 kilo electron Volts (keV) is detected. An energy level of 140.5 keV is typical of a gamma ray photon generated by Technetium-99. However, because of a number of factors, including manufacturing tolerances and variations in electronic component characteristics, an identically manufactured probe may generate an electronic pulse of 4.9 volts when detecting a gamma ray photon having an energy level of 140.5 keV. Further, even if the output of a particular probe is within acceptable tolerances at the factory, the output signal level may shift over time. When using probes which vary over time or from probe to probe, the control units must, therefore, be calibrated using a known radioactive source so that the electronic output signals from the probe are correctly interpreted by the radiation detection system.

Radiation detection systems are typically calibrated against a radioisotope which has a known peak energy level. This may be accomplished by, for example, calibrating each radiation detection system periodically in a biomedical lab. The probe is held near a radioisotope having a known, characteristic, gamma radiation energy level. Each gamma ray photon emitted by the radioisotope represents a singular radioactive event and each gamma ray photon has an energy level measurable in kilo electron volts (keV). Each such gamma ray photon or radioactive event which is detected by a probe may be referred to as a count. Upon detecting gamma ray photons, the probe generates a series of electric pulses, each pulse having a voltage which is proportional to the energy level of a gamma ray photon. Since the probe is positioned directly adjacent a radioactive source emitting gamma ray photons of a known energy level, the number of counts associated with that energy level would be far higher than the number of counts from other sources such as background radiation or Compton scatter. Thus, with the probe positioned near a known source, the control unit may be adjusted to calibrate the system by identifying the probe output signal (e.g. voltage) having the highest number of occurrences within a predetermined time period or by accepting a predetermined number of counts and identifying the output signal (e.g. voltage) associated with the largest number of counts. The output signal associated with the largest number of counts may then be interpreted to represent the energy level of the calibration radiation source. In order to calibrate a probe properly a statistically significant number of counts must be used. The predominant pulse height, also called the peak pulse height, can be derived from the recorded spectrum of pulses. The peak pulse height is interpreted by the radiation detection system to correspond to the known, characteristic energy level of the radioisotope used for calibration. Once the peak pulse height has been identified for a particular probe, the control unit input window may be set to allow that signal to pass while filtering out other signals such as noise or Compton scatter.

Normally, probes are designed and manufactured to have a predetermined output signal level for a count of a predetermined energy level. Unfortunately, a probe can lose calibration between the time it is calibrated in a lab and the time it is used on a patient. Calibration loss (drift) can also occur due to mishandling of delicate probes or during prolonged storage periods. In addition, the radioisotopes typically used in the calibration lab are not always the same as those used in the surgical patient (it is desired to inject a radioisotope with a short half-life into the patient, whereas the half-life of the radioisotope used in the calibration lab is preferably long so that it can be used over an extended period of time). Thus, the energy level of the radioisotope used to calibrate the radiation detection system may be different then the peak energy level of the radionucleide injected into the patient. Therefore, in current systems it may be necessary to provide some means for extrapolating the results of the laboratory calibration to the actual surgical situation. Although the individual contributions probe drift, control unit drift, probe damage, and using calibration radioisotopes are typically small, it is desirable to reduce or eliminate them altogether. It would, therefore, be desirable to calibrate the control unit to the output of a particular probe immediately before its use, and preferably with the same radionucleide used in the patient. The latter approach would be practical if the physician operator could perform the calibration immediately prior to the procedure. The physician operator, however, often does not have the expertise of a nuclear imaging technician, nor is the physician operator working in the controlled conditions of a biomedical laboratory. What is needed is calibration method which could be easily performed by the physician operator in the operating room. The calibration method could be made suitable for use by physician operators by automating many of the steps and by providing appropriate feedback signals to the operator in order to properly position the probe during the calibration procedure. It would, therefore, be advantageous if the radiation detection system could be calibrated using the radionucleide injection site. In particular, the injection site in a sentinel node procedure may be suitable for use as a calibration source because most of the injected radionucleide remains at the injection site for many hours after injection; the lymphatic system drains a relatively small amount during that time. Alternatively, it would be advantageous to design a calibration method which used a separate radioactive source available to the physician operator, such as the radionucleide in the administration syringe which is available to the physician operator immediately prior to the surgery.

In addition to the need for the radiation detection system to be properly calibrated, a filter is still required to discern radioactive emissions of the radionucleide in suspect tissue from background radiation. This background radiation, results predominately from Compton scattering. Compton scattering (or scatter) results from the interaction of gamma ray photons with electrons of body tissues. The scattered gamma ray photons have energies ranging from slightly below the full energy gamma ray photons down to and below typical x-ray energies (the "Compton continuum"). The apparent points of origin of these Compton scattered gamma ray photons have only a limited relationship to the site from which the unscattered, full energy gamma ray photons originated, and therefore have little relationship to the location of the tissue of interest. When using the method disclosed in U.S. Pat. No. 5,732,704, much of this Compton scatter comes from the radionucleide concentrated around the injection site in the patient, and this radiation can obscure the gamma radiation emitted by the radionucleide that has migrated to the sentinel node. Discerning the gamma radiation emitted by the radionucleide in the sentinel node from all other radiation sources reliably and consistently for each surgical patient is a highly desired objective of the surgeon. Therefore it is desirable to be able to discriminate between those gamma ray photons having energies close to that of the full-energy gamma ray photon and background radiation. Therefore, it is desirable to utilize a filter or window within the control unit which eliminates the probe output signals representative of background radiation. Normally the filter output includes the probe output signal levels representative of a full energy gamma ray photon and excludes probe output signal levels which are representative of background radiation, including undesirable radiation resulting from Compton scattering, such filters are known in the art.

The prior art discloses radiation detection devices that remove background radiation using "windowing techniques" in order to discern and process the gamma radiation emitted by the radionucleide concentrated in suspect tissue. U.S. Pat. No. 5,694,933 issued to Madden et al on Dec. 9, 1997 discloses an apparatus having a hand-held probe, a signal processor, and a multichannel control unit (MCA) to identify a peak energy level, to set manually a window of energy levels, and to perform a variety of other functions.

Another phenomenon associated with radiation detection systems is commonly known in the art as "pileup". Pileup occurs when the frequency of counts impinging on the forward window of the probe is higher than the response rate of the radiation detection system, especially the crystal and detector portion of the probe. Thus the system is unable to detect and process each count individually. As a result, a multiplicity of counts emitted by an especially "hot" radiation source may be detected as a smaller number of counts having a higher energy level. Pileup phenomena are of two general types, which have somewhat different effects on pulse height measurements. The first type is known as tail pileup and involves the superposition of pulses on the long-duration tail from a preceding pulse. A second type of pileup is called peak pileup and occurs when two pulses are sufficiently close together so that they are treated as a single pulse by the radiation detection system. These types of pileup lead to distortions of the recorded pulse height spectrum and can cause a misinterpretation of the emissions of the radionucleide during both the calibrating of the probe and the locating of the sentinel node. A detailed description of pileup is provided in Radiation Detection and Measurement, by Glenn F. Knoll, pages 610–612, publisher John Wiley and Sons, Inc, (hereinafter Knoll). Knoll further describes electronic and statistical means for "pileup rejection" (pages 612–620) in order to reduce but not totally eliminate the problems associated with pileup.

One method for reducing the effects of pileup is to position the probe farther away from the radioactive source. Radiation intensity is inversely proportional to the square of the distance from the radiation source. Therefore, the quantity of gamma ray photons from a particular source which impinge on the receiving window of the probe is reduced by moving the probe away from the source. It is difficult to properly calibrate the probe if it is not positioned correctly with respect to the calibration source. It would, therefore, be advantageous during calibration if a high-count, feedback signal is provided to the operator when the count frequency is high enough to result in a significant pileup distortion of the recorded spectrum. Then the operator may quickly reposition the probe-receiving window farther away from the radioactive source.

Another situation that may occur during calibration of a radiation detection system is when the operator does not position the receiving window of the probe close enough to the radioactive source. In accord with the inverse square law for radiation propagation, the resulting count frequency may be very low. If the count frequency is very low, the time required to detect a statistically significant number of counts may be high (several seconds). When count frequency is so low that it would take a significant length of time to collect the required number of counts, it would be advantageous to provide a low-count, feedback signal to the operator. Then the probe could be repositioned closer to the radioactive source. Furthermore, if the low-count feedback signal is generated when the count frequency is less than desired, and a high-count feedback signal is generated when count frequency is more than desired, then the operator is aided in positioning the probe receiving window the correct distance from the radioactive source. Finally, if a third feedback signal is generated when a desired count frequency is obtained (neither too high or too low), it would be even easier for the operator to correctly position the probe relative to the radiation source. Thus, it would be advantageous to design a radiation detection system having a calibration mode wherein the physician operator is assisted in positioning the probe during calibration of the radiation detection system. In such a system, the physician operator could calibrate the system during or immediately prior to initiating a surgical procedure.

The calibration positioning method described herein may be combined with an automatic windowing method for determining an energy acceptance window in order to reduce the effects of background radiation. An operator could use the combined methods to calibrate the radiation detection system using the injection site in the patient of the radionucleide as the radiation source. By using such a calibration method on the injection site, it would be practical to use low cost probes that generate a wide range of pulse magnitudes for counts of a given energy level. Also, the effects of calibration error due to electronic drift within the radiation detection system, damage to the probe during handling, and calibration on a different radioisotope may be diminished or avoided.

SUMMARY OF THE INVENTION

The present invention is a method of calibrating a radiation detection system by adjusting the parameters of a control unit for each probe attached to the control unit. The method described provides a reliable and practical way of using low cost radiation detection probes having variations in probe gain where probe gain is the ratio of voltage generated at the probe output for a given energy input. That is, probe gain is the factor which relates the energy deposited in a probe by a gamma ray photon to the voltage generated at the output of the probe where the voltage is generated as a result of the photon striking the detector input.

A method according to the present invention uses feedback to ensure that the user has an appropriate count rate to accurately calibrate the system. The method comprises the following steps: An operator positions a radiation detection probe near a calibration radiation source, such as the surgical injection site of a radionucleide. Then the radiation detection probe generates a plurality of electronic pulses, each of the electronic pulses having a pulse magnitude proportional to the energy level of a count. Next the radiation detection system calculates a pulse frequency. The radiation detection system generates a low-count feedback signal when the pulse frequency is less than a predetermined low-count frequency. The radiation detection system generates a high-count feedback signal when the pulse frequency is greater than a predetermined high-count frequency. The radiation detection system generates an optimal-count feedback signal when the pulse frequency is greater than or equal to the predetermined low-count frequency and is less than or equal to the predetermined high-count frequency. Each of the feedback signals may be an audible feedback signal, a visual feedback signal, or both. When the probe is positioned such that the optimal feedback signal is generated, the control unit begins to collect and record outputs from the probe. The control unit continues to collect and record output signals from the probe until a statistically significant number of output pulses have been recorded. The control unit then categorizes the plurality of pulses into a plurality of pulse magnitude ranges. Next the control unit determines the number of pulses categorized in each of the plurality of pulse magnitude ranges. The control unit then identifies the pulse magnitude range containing the most pulses and labels that range the peak pulse magnitude range. Then the system assigns an energy level to each of the plurality of pulse magnitude ranges. The energy level assigned to the peak pulse magnitude may be referred to as the characteristic energy level and is generally the characteristic energy level of gamma ray photons emitted by the calibration source. Once calibrated, the control unit may use the characteristic energy level for a plurality of purposes. For example, the control unit may determine the lower cut off limits of an energy acceptance filter which includes the characteristic energy level but excludes pulses representative of gamma ray photons having energy levels below a predetermined threshold energy level. The threshold energy level generally has a predetermined relationship to the characteristic energy level. The radiation detection system thereafter processes only pulses corresponding to an energy level passed by the energy acceptance filter. In another embodiment of the present invention, the energy acceptance filter also passes pulse representative of gamma ray photons having energy levels up to a highest energy level having a second predetermined relationship to the characteristic energy level.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

Figure 1:
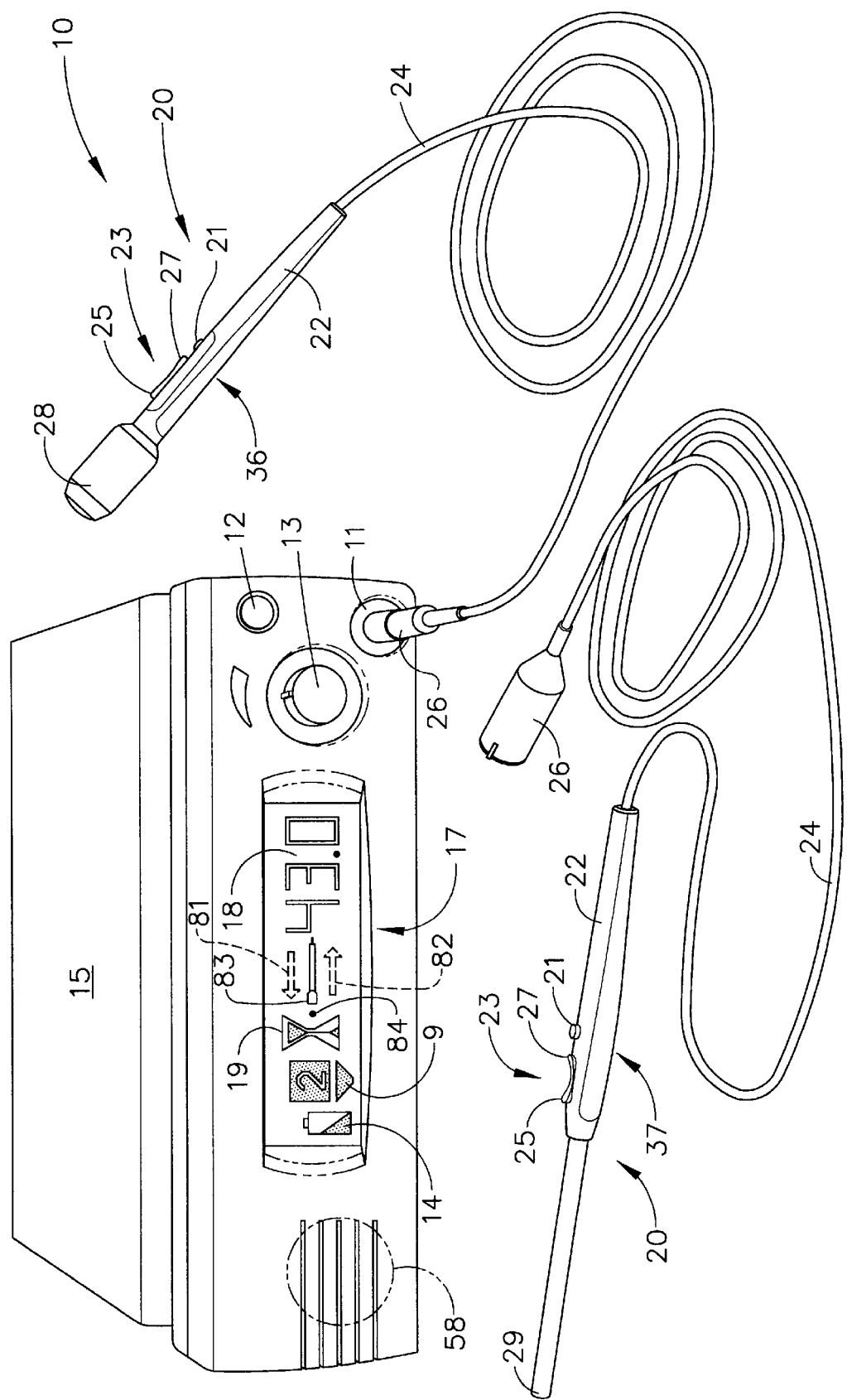
FIG. 1 shows a radiation detection system comprising a scanning probe, a targeting probe, and a control unit.

FIG. 1 is a perspective view of a radiation detection system 10 in accordance with one embodiment of the present invention. Radiation detection system 10 comprises a control unit 15, a scanning probe 36, and a targeting probe 37. Scanning probe 36 includes a scanning detector assembly 28. Targeting probe 37 includes a targeting detector assembly 29. Scanning probe 36 and targeting probe 37 may also be generally referred to as a probe 20. Probe 20 further comprises a probe housing 22, a cable 24, and a connector 26. Probe housing 22 includes a mode button 21 and an audio range switch 23. Audio range switch 23 includes a range up button 25 and a range down button 27. In FIG. 1, control unit 15 further includes a volume set button 12, a volume knob 13, a cable input 11, and a display 17. Display 17 includes a visual count rate indicator 18, a wait indicator 19, a range indicator 9, probe indicator 83, left arrow 81, right arrow 82 and a battery indicator 14. A more detailed description of a radiation detection system is provided in U.S. patent application Ser. No. 09/266,961 which was previously incorporated herein by reference.

Figure 2:
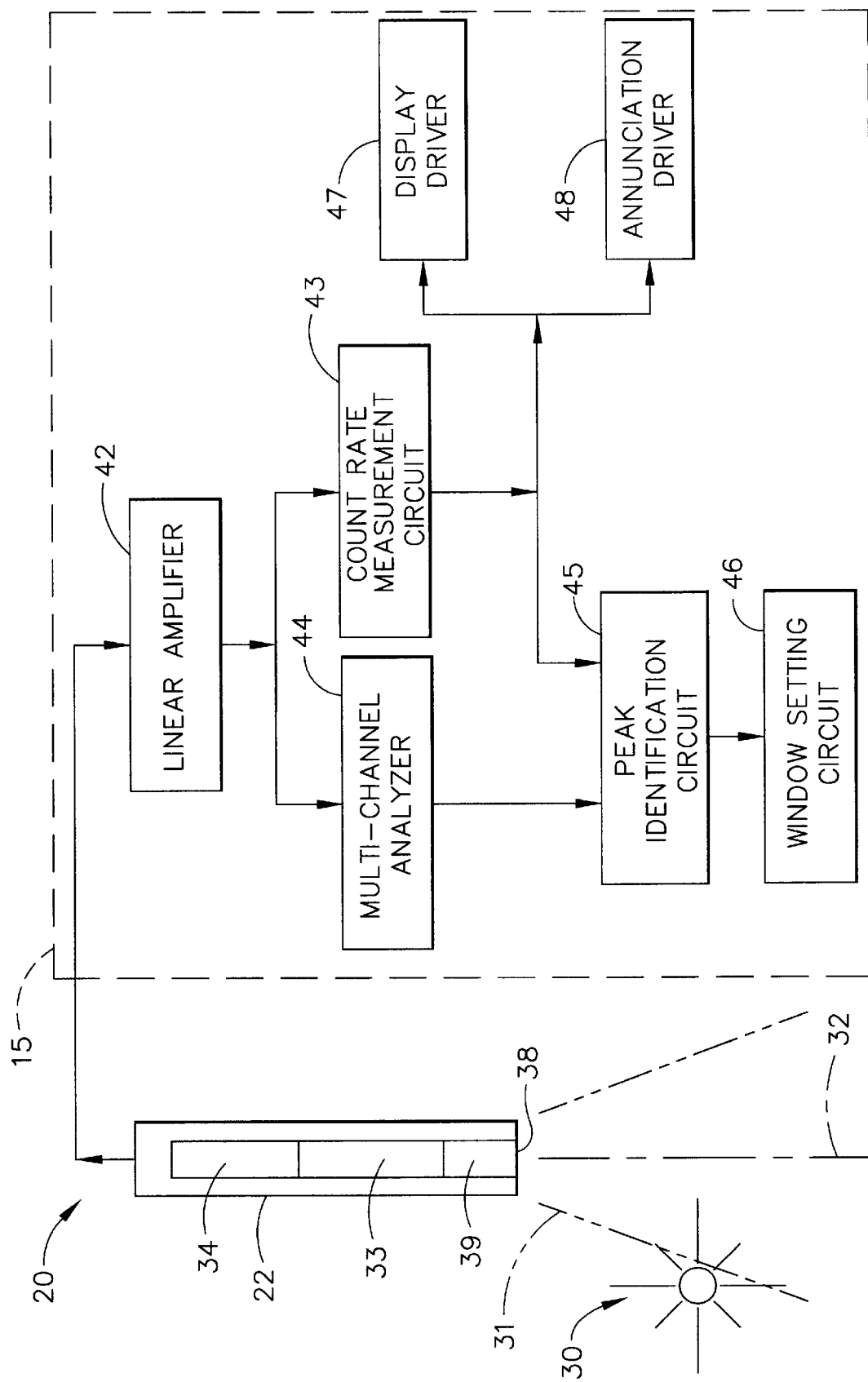
FIG. 2 is a block diagram of a portion of the radiation detection system shown in FIG. 1.

FIG. 2 is a block diagram of probe 20 and a block diagram of one embodiment of probe 20 and control unit 15. In the block diagram of FIG. 2, control unit 15 is in its calibration mode. Probe 20 comprises housing 22 sealably containing a columnator 39, a detector 33 and a preamplifier/switch assembly 34. Probe 20 may be multi-patient use reusable and resterilizable instrument, or, alternately, be a single patient use disposable instrument. A suitable probe 20 may be purchased from Neoprobe, Inc. as a Model 1017 14 mm reusable probe. Probe 20 may also be partially disposable such as, for example, when detector 33 is detachable from probe 20 and is reusable/resterilizable and the remainder of probe 20 is disposable. Probe 20 is configured to be positioned by a physician operator closely adjacent the site of a radiation source 30 which may be, for example, a radion-electrode injection site. Probe 20 detects gamma ray photons emitted by radiation source 30 and other background radiation sources lying within a field-of-view 31 approximately centered on a longitudinal axis 32 of probe 20. Field-of-view 31 is also referred to as a "solid angle of acceptance" and is established by the size, depth, and shape of columnator 39.

One embodiment of preamplifier/switch assembly 34 of probe 20 includes a printed circuit board (not shown), mode button 21, range down button 27 and range up button 25 are shown in FIG. 1. Preamplifier/switch assembly 34 amplifies each electronic signal received from detector 33 to a voltage magnitude that can be transmitted to control unit 15 via cable 24. All signals (including noise) from probe 20 are proportionally amplified and shaped into pulses in a linear amplifier 42 of control unit 15. In this embodiment, the resulting pulse magnitudes are in the range of, for example, approximately 0–5 volts. A count rate measurement circuit 43 counts the pulses generated by linear amplifier 42 over a time interval of, for example, 64 milliseconds. As one example, count rate measurement circuit 43 may calculate a running average of the pulses generated by linear amplifier 42 to generate a prevailing count rate. The prevailing count rate determined by count rate measurement circuit 43 increases dramatically when probe 20 is positioned very close to radiation source 30, and conversely, decreases to a very small rate when probe 20 is very far from radiation source 30. The distance between probe 20 and radiation source 30 should be optimized during calibration to minimize effects detrimental to the calibration process. As already described, detrimental effects include the long time to obtain a statistically significant number of pulses for peak identification where probe 20 is too far from radiation source 30 and the phenomena associated with pileup where probe 20 is too close to radiation source 30. Therefore, control unit 15 is equipped with a means to cue the operator as to positioning probe 20 in the optimal distance range. A display driver 47 drives display 17 to provide the physician operator with visual cues. An annunciator driver 48 drives an annunciator 58 to provide the physician operator with audible cues. Either one or both of the visual and audible cues may be provided for using the calibration method of the present invention. Count rate measurement circuit 43 is programmed to provide a first feedback signal to peak identification circuit 45, display driver 47 and annunciator driver 48 when the measured count rate is below a predetermined low-count frequency. Measurement circuit 43 is programmed to provide a second feedback signal to peak identification circuit 45, display driver 47 and annunciator driver 48 when the measured count rate is above a predetermined high-count frequency. Control measurement circuit 43 is programmed to provide a third feedback signal to display driver 47 and annunciator driver 48 when the measured count rate is greater than or equal to the predetermined low-count frequency and is less than or equal to the predetermined high-count frequency.

The first, second, and third feedback signals may include visual cues. For example as illustrated in FIG. 1, during calibration, display 17 may show a representation 83 of probe 20 positioned horizontally with receiving end 38 pointed at a circle 84 representing a point radiation source. The first feedback signal may include a left arrow 81 on display 17 pointing towards the circle 84, thus cueing the operator to move probe 20 closer to the radiation source. The second feedback signal may include a right arrow 82 on display 17 pointing away from circle 84, thus cueing the operator to move probe 20 away from radiation source 30. For the third feedback signal, the arrow on display 17 may disappear and wait indicator 19 may then appear, indicating the relative time remaining to complete calibration while probe 20 is held an optimal distance from radiation source 30. Similarly, audibly distinct tones may be provided for each of the first, second, and third feedback signals. In one embodiment, a low-pitch intermittent tone is provided for the first feedback signal, a high-pitch intermittent tone is provided for the second feedback signal, and a middle-pitch steady tone is provided for the third feedback signal.

In FIG. 2, control unit 15 further includes a multi-channel analyzer 44, also referred to as an MCA 44. A suitable MCA 44 may be a Microace MCA which may be purchased from a EG&G Ortec, Inc. MCA 44 stores in memory each pulse it receives from linear amplifier 42 during the sampling period and assigns each of those individual pulses to a particular channel within MCA 44 based on the pulse magnitude (e.g. voltage). Each such channel is representative of a particular pulse range which, in turn is representative of a particularly energy range. As additional counts are detected by probe 20 they are distributed into the various channels in MCA 44. This distribution of counts into various channels constitutes a spectrum or histogram of received pulse magnitudes which are, in turn, representative of the energy content of the detected photons. The software in MCA 44 may be written specifically to perform various functions including rejection of low level pulses, digitizing received pulses, and creation of a histogram of the received pulses. Suitable software is available from EG&G Ortec, Inc. as its MARSTRO-32 MCA Emulator software. MCA 44 may include a microcontroller, and an analog-to-digital converter (ADC) for converting pulse voltages (for example, 0–5 volts) into digital numbers (for example, 0–4096 bits) that can be read by the microcontroller. MCA 44 may further include a discriminator and reset delay device that is set by the microcontroller to reject low level pulse magnitudes which result from electronic noise or very low level radiation and to prevent pulses from reaching the ADC while it is converting an earlier pulse. With the discriminator and reset delay of MCA 44, the ADC processes pulses having magnitudes in the range of interest. The MCA 44 may also include a sample and hold device to hold a pulse during the time it takes to access the ADC.

Figure 5:
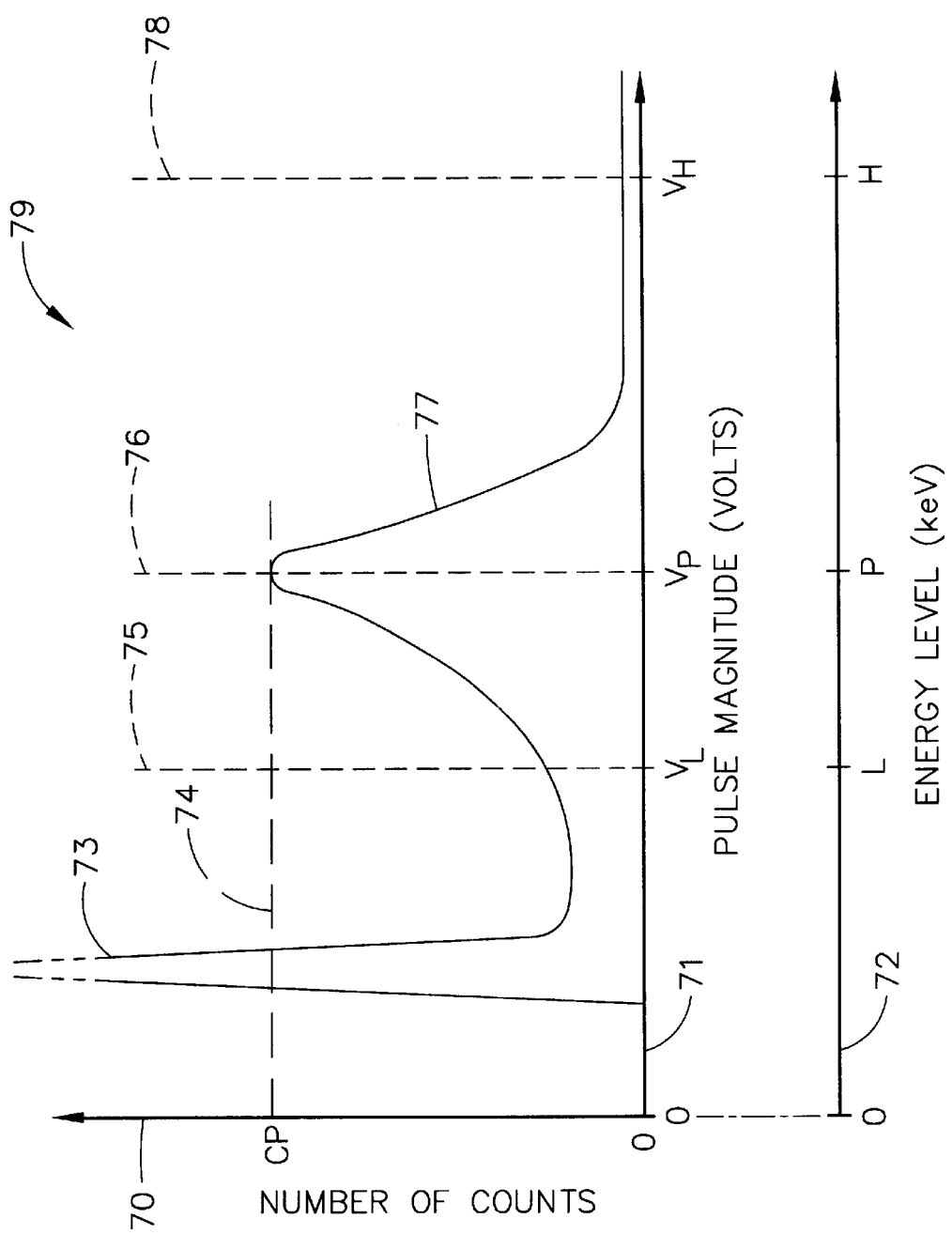
FIG. 5 is an example of a pulse spectrum as it may be recorded by the radiation detection system of FIG. 1.

FIG. 5 shows a typical spectrum plot 79 of energy levels of gamma ray protons received by probe 20 and corresponding probe output voltages for a radioisotope such as Technetium-99. Spectrum plot 79 represents graphically the accumulation of counts detected from the radioisotope by probe 20 over a fixed time period, and includes a full-energy gamma ray peak 77 and a low level energy peak 73. Low level energy peak energy peak 73 may be caused by electronic noise and low level background radiation. The nonzero spectrum between energy peaks is a result of a number of factors, including Compton scattering. In FIG. 5, vertical axis 70 represents the number of counts accumulated within a given time period at a given energy. In FIG. 5, first horizontal axis 71 represents voltage accumulated Second horizontal axis 72 represents the energy level of accumulated counts in units of kilo electron volts (KeV). Full-energy gamma ray peak 77 has a maximum number of accumulated counts at pulse magnitude 76. The voltage ($V_p$) may, therefore, be associated with the known energy level ($E_p$). For example, the energy level of gamma ray photons emitted by Technetium-99 is 140.5 keV. Therefore, if Technetium-99 is used as the calibration source voltage $V_P$ would be assigned to an energy level of 140.5 KeV. Once that assignment was made, output pulses from probe 20 having a voltage of $V_P$ would be interpreted by control unit 15 as having been generated by a gamma ray photon having an energy level of 140.5 KeV.

The output of MCA 44 is provided to a peak identification circuit 45. Peak identification circuit 45, which may be implemented in software in MCA 44, is designed to identify the characteristic full-energy gamma ray peak. As an example, the software resident in the microcontroller of MCA 44 which may be, for example, the MAESTRO-32 software mentioned previously, may be used to identify the full energy gamma ray peak The peak is identified by comparing the number of counts recorded in each pulse magnitude range to the number of counts in the other pulse magnitude ranges and selecting the pulse magnitude range or ranges with the highest number of counts. Then the center point of the range or ranges is determined and used as $V_P$. Once a pulse magnitude is assigned to the energy of the gamma ray photons emitted by radiation source 30, the calibration is complete.

The output of the peak identification circuit 45 may be provided to a window setting circuit 46, which may also be implemented by suitable software resident in control unit 15. Window setting current 46 establishes the lowest and highest limits energy limits so as to establish the width of the energy acceptance window encompassing the characteristic full-energy gamma ray peak. When the energy acceptance window has been set, a fourth feedback signal is provided to alert the operator that the calibration of probe 20 is complete. The fourth feedback signal may comprise, for example, a short audible beep. Fourth feedback signal may also comprise a visual cue. For radiation detection system 10 in FIG. 1, wait indicator 19 on display 17 indicates completion of the calibration method by changing to an "emptied" hourglass.

Figure 3:
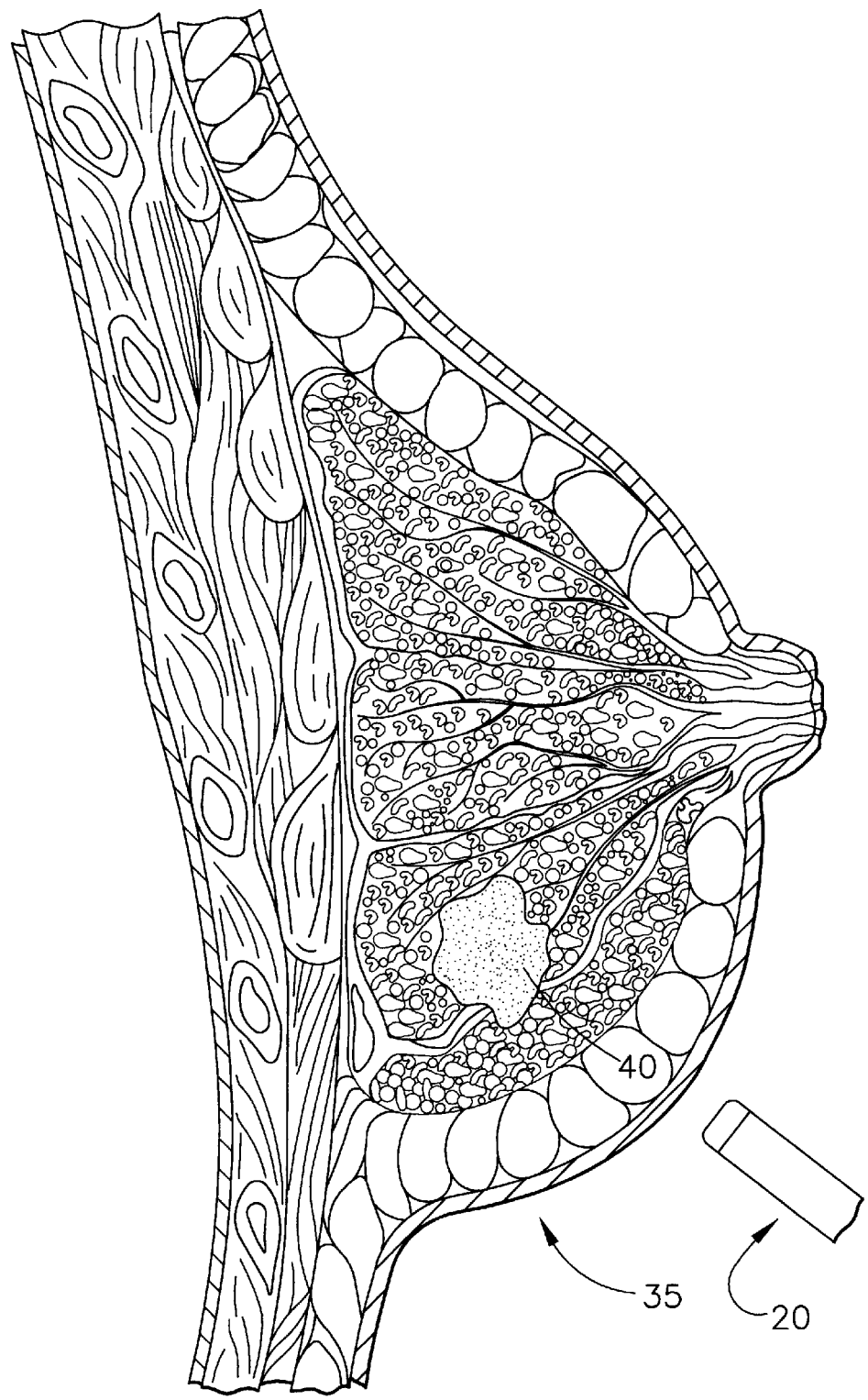
FIG. 3 is a sagittal section view of the breast of a surgical patient.

A physician operator may, therefore, quickly calibrate the radiation of electron system for a particular probe. To calibrate the radiation detection system the physician operator places the control unit in calibration mode by, for example, processing one or more of the buttons on probe 20. By using the feedback signals described previously, the operator may quickly and accurately position probe 20 an optimal distance from radiation source 30 which is a known radioisotope. Since the positioning of probe 20 is quick and simple, it is possible for the physician operator to calibrate the system immediately prior to a surgical procedure. Furthermore, the calibration may be performed using the radioisotope used in the surgical procedure. FIG. 3 shows a breast 35 of a surgical patient. A probe 20 is positioned near an injection site 40 of a known radionucleide. The radionucleide containing, for example, Technetium-99, has been injected near a tumor previously located during a biopsy procedure. The radionucleide enters the lymphatic system surrounding the tumor and a portion of it migrates to the sentinel node. A high concentration of the radionucleide remains concentrated around the injection site for at least several hours as the injected radionucleide decays and is distributed throughout the patient's body. During this time it is possible to obtain an accurate calibration of probe 20 at the injection site using the calibration method of the present invention.

Figure 4A:
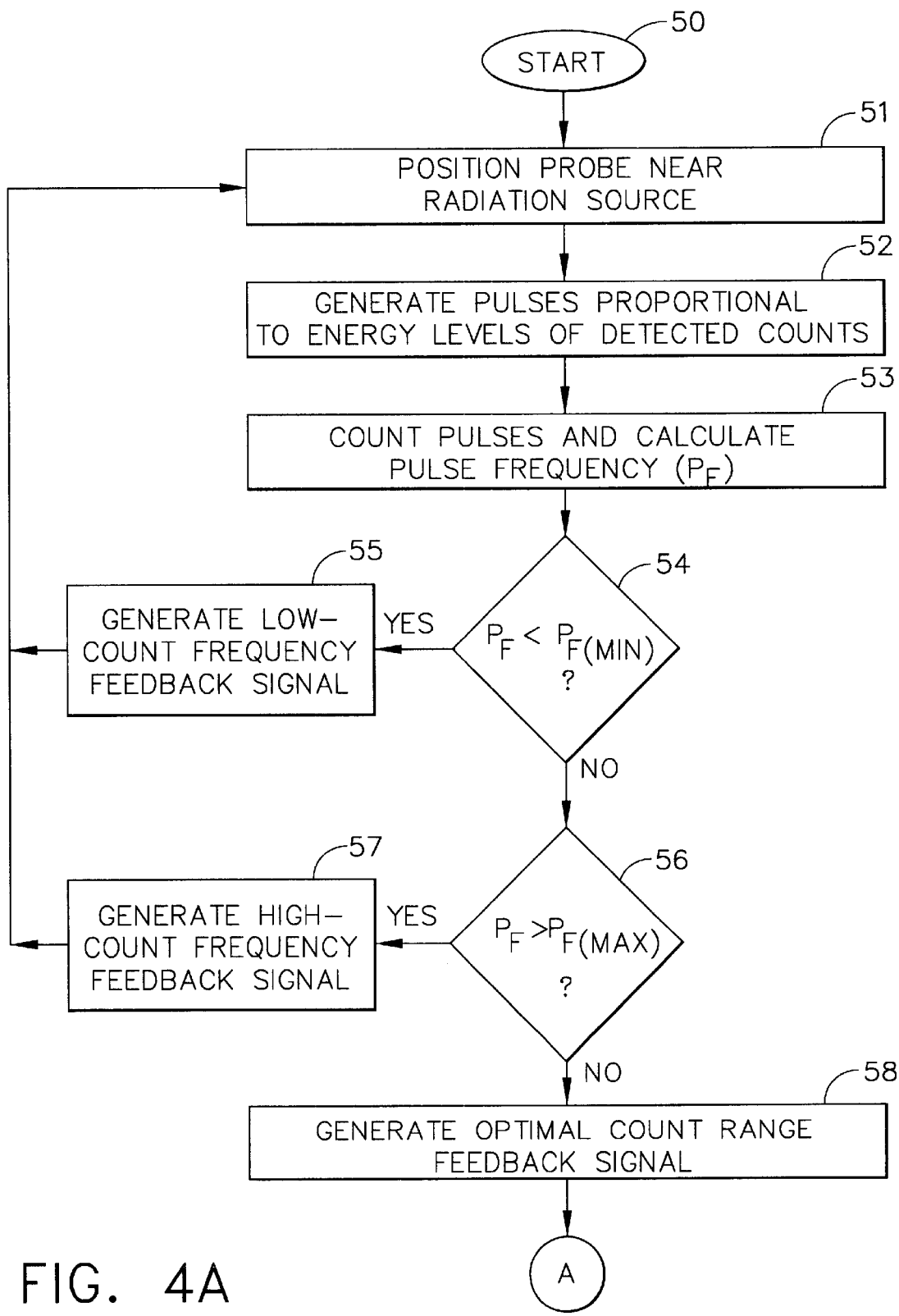
FIG. 4A is a first portion.
Figure 4B:
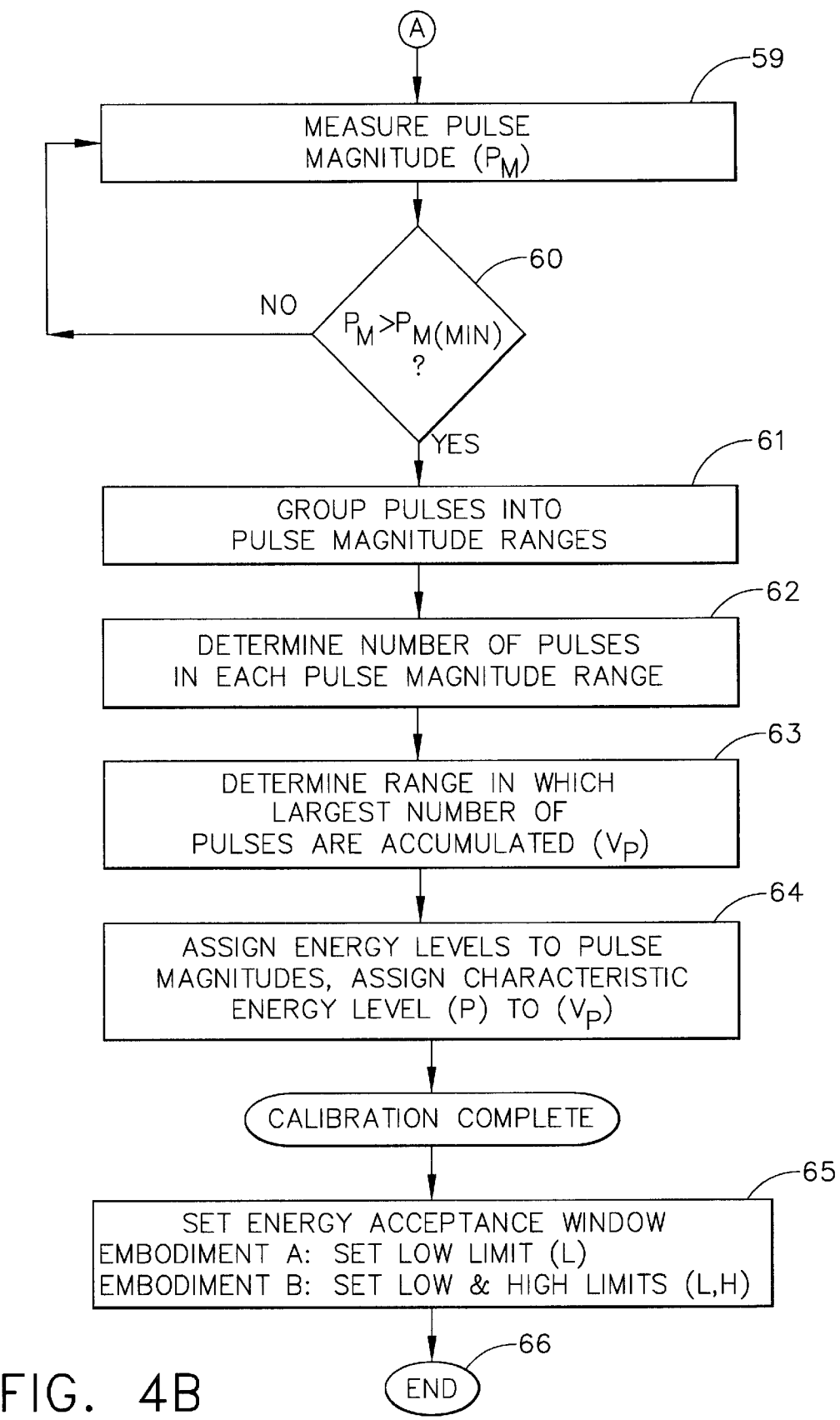
FIG. 4B is a second portion of a flowchart that describes a method of calibrating a probe of a radiation detection system such as shown in FIG. 1.

The calibration method of the present invention is shown in a flowchart in FIGS. 4A and 4B. The first portion of the flowchart (FIG. 4A) and the second portion of the flowchart (FIG. 4B) are divided at a circled letter "A". The calibration method begins at Step 50 once the operator has powered-up radiation detection system 10 and established the radiation source (for example, the injection site of radionucleide) to perform the calibration. Next, in Step 51, the operator positions probe 20 near the radiation source such as shown in FIG. 3 and initiates the calibration mode by, for example, pressing one or more of the buttons on probe 20 in a predetermined sequence. Probe 20 may be held by the operator's hand, or may be fixed in a holding fixture having adjustment features necessary to reposition probe 20 as required. In Step 52, probe 20 generates output pulses that are proportional to the energy levels of the counts. In Step 53, count rate (also referred to as pulse frequency, $P_F$) is calculated. The calibration method then proceeds to Step 54 to test whether the measured pulse frequency $P_F$ is less than a predetermined, minimal pulse frequency $P_{F(MIN)}$. A suitable value for $P_{F(NIN)}$ is approximately 100 counts per second, although $P_{F(MIN)}$ may have different values. If pulse frequency measured is less than predetermined minimal pulse frequency, then control unit 15 generates a low-count frequency feedback signal in Step 55. This alerts the operator to position probe 20 closer to radiation source 30 or to redirect receiving end 38 (see FIG. 2) so that the radiation source is within the field-of-view 31 of probe 20. If pulse frequency $P_F$ is greater than a predetermined maximal pulse frequency $P_{F(MAX)}$ in Step 56, then control unit 15 generates a high-count frequency feedback signal in Step 57. The operator may then reposition probe 20 farther from the radiation source. A suitable value for $P_{F(MAX)}$ is approximately 4000 counts per second, although $P_{F(MAX)}$ may have different values. If the measured pulse frequency is in an optimal range for calibration as calculated in Step 58, control unit 58 generates an optimal count range feedback signal. The operator then simply maintains the position of probe 20 until calibration is complete at Step 66. Once calibration is complete, and while probe 20 is positioned at an optimal distance from the radiation source, control unit 15 automatically, within about 2 to 11 seconds for example, performs steps 59–65 to determine and set an energy acceptance window.

In step 59 count rate measurement circuit 43 counts pulses from linear amplifier 42 and MCA 44 measures the pulse magnitude of each pulse. The number of pulses counted is $P_M$. Then in step 60, pre-programmed MCA 44 insures that a statistically significant number of pulse magnitudes is recorded, or $P_M$ is greater than $P_{M(MIN)}$, where $P_{M(MIN)}$ is a predetermined minimal number of pulse magnitudes. Step 60 insures that enough pulses have been recorded such that when they are assigned to pulse magnitude ranges, enough data exists within each range to compare the number of pulse magnitudes in each range. As more pulses are sampled, the error associated with the random distribution is reduced. A suitable value for $P_{M(MIN)}$ is approximately 1000 counts, although other values for $P_{M(MIN)}$ may be used with the present invention. In Step 61, the recorded pulses are grouped into channels or pulse magnitude ranges, thus forming a histogram as described previously. Analytical methods for forming a histogram comprising a plurality of pulse magnitude ranges (sometimes called channels) representing energy levels are known in the art (see U.S. Pat. No. 5,694,933). In the present invention, each pulse magnitude range has a common, predetermined width depending on the full-energy gamma ray peak magnitude of the radioisotope used for the calibration procedure. If the radioisotope used in the calibration is Technetium-99 having a full-energy gamma ray peak magnitude of 140.5 kiloelectron volts (keV), then a useful width of each pulse magnitude range is 2 keV, providing about seventy pulse magnitude ranges. In Step 62, the number of pulses in each pulse magnitude range is determined and in Step 63, a peak pulse magnitude range ($V_P$) is determined as described previously Peak pulse magnitude range ($V_P$) is the pulse magnitude range having the most recorded pulses.

Enhancements to the present invention will occur to those skilled in the art. For example, a calibration method according to the present invention may use a number of qualifiers to ensure that the selected pulse magnitude range is representative of a true full-energy gamma peak (having a magnitude easily discernible from the rest of the spectrum plot). In general, a qualifier is a set of conditions programmed into MCA 44, wherein each pulse must meet the set of conditions to be further processed. Qualifiers would be advantageous during the calibration method if, for example, probe 20 was not pointed directly at the radiation source, but pulse frequency was high enough to proceed with the method. If probe 20 was not pointed at the radiation source, none of the full-energy gamma ray photons would impinge directly on detector 33, and therefore control unit 15 would not accurately record a full-energy peak but might record a high number of counts in a particular range, giving a false peak. Rather, a relatively flat spectrum plot would be obtained, except for the peaks associated with noise and background radiation. In such a situation, if the histogram did not fit a predetermined characteristic curve the operator could be alerted (by audible or visual feedback signals) to redirect probe 20 so that radiation source 30 is within field-of-view 31 of probe 20.

In step 64 of FIG. 4B, the known, characteristic, full-energy level for the radioisotope used in the calibration is assigned to correspond with the center voltage in the peak magnitude range. The remaining pulse magnitude ranges are then assigned lower energy levels, although counts falling within these lower energy pulse magnitude ranges are not necessarily weighted as equal to the full energy level pulse magnitude ranges. A non-proportional assignment of weighting counts within these pulse magnitude ranges may be used, for example, to increase the sensitivity to higher energy level pulse magnitudes, thus improving the ability of radiation detection system 10 to discern from which direction the detected radiation of interest is coming. Once Step 65 is complete, the system calibration is complete.

Once the system calibration is complete, other system parameters may be set. In step 65 for one embodiment (A) of the present invention, control unit 15 automatically sets an energy acceptance window having only a lowest energy level L (see FIG. 5) having a predetermined mathematical relationship to the peak energy level P. For example, the lowest energy level L may be set to be a predetermined percentage of the peak energy level P. For the radiation detection system of FIG. 1, a lowest energy level L that is, for example, about 78.2% of the peak energy level P approximately represents detection of only those gamma ray photons impinging at less than a 90 degree angle to field-of-view 31.

In step 65 for another embodiment (B) of the present invention, control unit 15 automatically sets an energy acceptance window having both a lowest energy level L and a highest energy level H (see FIG. 5), each having a predetermined mathematical relationship to the peak energy level P. This embodiment may be desirable, for example, if a radioisotope with multiple energy peaks is being surveyed.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that only the spirit and scope of the appended claims limit the invention.

What is claimed is:

1. A method for calibrating a radiation detection system for use in a medical procedure, the method comprising the steps of:
    a) positioning a probe of said radiation detection system with respect to a patient injection site of a radionuclide;
    b) obtaining feedback responsive to radiation detected at the probe position;
    c) repositioning the probe in response to the feedback; and
    d) calibrating the radiation detection system using radiation obtained with the repositioned probe.

2. The method of claim 1 wherein the feedback comprises an audible feedback signal.

3. The method of claim 1 wherein the feedback comprises a visual feedback signal.

4. The method of claim 1 wherein the feedback comprises a low-count feedback signal.

5. The method of claim 1 wherein the feedback comprises a high-count feedback signal.

6. The method of claim 1 wherein the step of repositioning the probe comprises repositioning the probe to obtain an optimal-count feedback signal.

7. A method for us in calibrating a radiation detection system using radiation received from a patient injection site, the method comprising the steps of:
    a) determining a frequency responsive to radiation received at a position spaced from the patient injection site;
    b) providing feedback responsive to the frequency determined in step a);
    c) repeating steps a) and b) until the feedback of step b) is a desired feedback; and
    d) calibrating the radiation detection system using radiation received at a position for which the feedback of step b) is the desired feedback.

8. The method of claim 7 wherein the step of providing feedback comprises providing an audible feedback signal.

9. The method of claim 7 wherein the step of providing feedback comprises providing a visual feedback signal.

10. The method of claim 7 wherein the step of providing feedback comprises providing a low-count feedback signal.

11. The method of claim 7 wherein the step of providing feedback comprises providing a high-count feedback signal.

12. The method of claim 7 wherein the step of providing feedback comprises providing an optimal-count feedback signal.

13. A method for use in calibrating a radiation detection system using radiation received from a patient injection site, the method comprising the steps of:
    a) determining a pulse frequency responsive to radiation received at a position spaced from the patient injection site;
    b) providing a low-count feedback signal when said pulse frequency is less than a predetermined low-count frequency;
    c) providing a high-count feedback signal when said pulse frequency is greater than a predetermined high-count frequency;
    d) providing an optimal-count range feedback signal when said pulse frequency is greater than or equal to said predetermined low-count frequency and is less than or equal to said predetermined high-count frequency; and
    e) calibrating the radiation detection system once the optimal-count range feedback signal is provided.

14. The method of claim 13 wherein the step of calibrating comprises:
    measuring a plurality of pulse magnitudes when said optimal-count range feedback signal is provided; and
    grouping said plurality of pulse magnitudes into a plurality of pulse magnitude ranges.

15. The method of claim 14 where in the step of calibrating further comprises:
    determining the number of pulse magnitudes corresponding to each of said plurality of pulse magnitude ranges;
    determining a peak pulse magnitude range from said plurality of pulse magnitude ranges, whereby said peak pulse magnitude range has the maximum number of corresponding pulse magnitudes; and
    assigning an energy level to each of said plurality of pulse magnitude ranges, whereby a peak energy level having a known, characteristic value according to said radiation source is assigned to said peak pulse magnitude range, and remaining pulse magnitude ranges are assigned energy levels that are lower than said peak energy level.

16. The method of claim 13 wherein the step of calibrating comprises setting an energy acceptance window wherein said radiation detection system processes only pulses corresponding to an energy level falling within the energy acceptance window.

* * * * *